United States Patent [19]

King et al.

[11] Patent Number: 5,432,610
[45] Date of Patent: Jul. 11, 1995

[54] DIODE-PUMPED POWER BUILD-UP CAVITY FOR CHEMICAL SENSING

[75] Inventors: David A. King, Palo Alto; William F. Carlsen, Oakhurst, both of Calif.; Damien F. Gray, Austin, Tex.; Richard J. Pittaro, San Carlos, Calif.

[73] Assignee: Hewlett-Packard Company, Palo Alto, Calif.

[21] Appl. No.: 228,317

[22] Filed: Apr. 15, 1994

[51] Int. Cl.$^6$ .................... G01N 21/00; H01S 3/098
[52] U.S. Cl. .................... 356/432; 356/301; 372/18; 372/75; 372/49
[58] Field of Search ............... 356/432, 436, 437, 438, 356/440, 300, 301, 302, 308, 318, 335–343; 372/18, 49, 43, 45, 96, 21, 75, 102

[56] References Cited

U.S. PATENT DOCUMENTS

| | | | |
|---|---|---|---|
| 4,435,808 | 3/1984 | Javan | 372/29 |
| 4,648,714 | 3/1987 | Benner et al. | |
| 4,884,276 | 11/1989 | Dixon et al. | |
| 4,907,237 | 3/1990 | Dahmani et al. | |
| 4,914,658 | 4/1990 | Stankov et al. | 372/18 |
| 5,038,352 | 8/1991 | Lenth et al. | |
| 5,108,931 | 4/1992 | Barrett et al. | 356/437 |
| 5,351,121 | 9/1994 | Baer et al. | 356/440 |

OTHER PUBLICATIONS

Satoshi Arimoto et al. "150 mW Fundamental-Transverse-Mode Operation of 670 nm Window Laser Diode", vol. 29 (6), pp. 1874–1879, *IEEE Journal of Quantum Electronics*, Jun. 1993.

V. M. Baev et al. "Intra-Cavity Spectroscopy with Diode Lasers", vol. B55, pp. 463–477, *Applied Physics B*, Aug. 1992.

Peter Buch et al. "Optically Self-Locked Semiconductor Laser with Servo Control for Feedback Phase and Laser Current", vol. 27 (7), pp. 1863–1868, *IEEE Journal of Quantum Electronics*, Jul. 1991.

B. Dahmani et al. "Frequency stabilization of semiconductor lasers by resonant optical feedback", Nov. 1987, vol. 12 (11), pp. 876–878, *Optics Letters*.

Wolfgang Demtröder. *Laser Spectroscopy*, Springer-Verlag, Berlin, 1982, pp. 390–395.

G. J. Dixon et al. "432-nm source based on efficient second-harmonic generation of GaAlAs diode-laser radiation in a self-locking external resonant cavity", vol. 14 (14), pp. 731–733, *Optics Letters*, Jul. 1989.

G. Eisenstein et al. "High quality antireflection coatings on laser facets by sputtered silicon nitride", Jan. 1984, vol. 23 (1), pp. 161–164, *Applied Optics*.

W. J. Kozlovsky et al. "Resonator-enhanced frequency doubling in an extended-cavity diode laser", 1993, pp. 172–175, *Proceedings of the Compact Blue-Green Lasers Topical Meeting*.

(List continued on next page.)

*Primary Examiner*—Hoa Q. Pham
*Attorney, Agent, or Firm*—Jeffrey Slusher

[57] ABSTRACT

A semiconductor laser power build-up system includes a semi-conductor laser. An optical resonance cavity is defined between at least two reflective elements and has an intracavity light beam along an intracavity beam path. A return light beam, which is a portion of the intracavity light beam, is transmitted through one of the reflective elements and is coincident with but oppositely directed relative to the incident beam. The laser is wholly optically locked to the cavity and the intracavity beam passes substantially without loss within the cavity. In a preferred application, a sample is placed in the cavity and a detector is provided to sense chemicals in the sample by, for example, detecting Raman-scattered light. A wavelength-determining element such as a grating or an etalon is preferably in the incident beam path between the laser and the cavity. The reflective elements can have very low transmission losses, an emission facet of the laser can have very low reflectivity, and feedback into the laser may be strong, for example, above 3%. When the laser is a diode laser, the invention provides for driving the diode laser with a current that is less than its bare-diode threshold current.

39 Claims, 3 Drawing Sheets

OTHER PUBLICATIONS

Ross Parke et al. "2.0W CW, Diffraction-Limited Operation of a Monolithically Integrated Master Oscillator Power Amplifier", vol. 5 (3), pp. 297–300, *IEEE Photonics Technolgy Letters*, Mar. 1993.

Hui Rong-Qing et al. "Improved Rate Equation Cavity Semiconductor Lasers", Jun. 1989, vol. 25 (6), pp. 1580–1584, *IEEE Journal of Quantum Electronics*.

Harold R. Simonsen. "Frequency Noise Reduction of Visible InGaAlP Diodes by Different Optical Feedback Methods", vol. 29 (3), pp. 877–884, *IEEE Journal of Quantum Electronics*, Mar. 1993.

Carol E. Tanner et al. "Atomic beam collimation using a laser diode with a self-locking power-buildup cavity", vol. 13 (5), pp. 357–359, *Optics Letters*, May 1988.

Yoshiyasu Ueno et al. "30-mW 690-nm High-Power Strained-Quantum-Well AlGaInP Laser", Jun. 1993, vol. 29 (6), pp. 1851–1856, *IEEE Journal of Quantum Electronics*.

Carl E. Wieman et al. "Using diode lasers for atomic physics", Jan. 1991, vol. 62 (1), pp. 1–20, *Rev. Sci. Instrum*.

Anthony E. Siegman, *Lasers*, University Science Books, Mill Valley, California, 1986, pp. 428–431.

A. Hemmerich et al. "Second-harmonic generation and optical stabilization of a diode laser in an external ring resonator", vol. 15 (5), pp. 372–374, *Optical Letters*, Apr. 1990.

DIODE-PUMPED POWER BUILD-UP CAVITY FOR CHEMICAL SENSING

BACKGROUND OF THE INVENTION

1. Field of the Invention

This invention involves optical systems for the detection of chemicals, in particular, to a self-locking optical cavity that generates an optical signal in response to the presence of a chemical analyte.

2. Description of the Related Art

The sensitivity and dynamic range of optical techniques make them well suited for use in chemical sensing systems. Accordingly, several sensing devices are now available that attempt to put these properties to use.

In any optical sensing system, the light source is a critical component. In choosing a light source, the designer must typically make a trade-off among the often conflicting requirements for high optical power levels, high efficiency, low cost, small size, and structural strength. One particularly advantageous development in this regard is that progress in solid state technology has led to the miniaturization of coherent light sources from meters (such as argon ion or helium-neon lasers) to microns (such as surface emitting quantum well laser diodes). For example, solid state diode lasers are now commercially available with output powers ranging from milliwatts to watts. An example of such a device is described in Parke, R., et al., "2.0 W cw, diffraction-limited operation of a monolithically integrated master oscillator power amplifier," IEEE Photon. Tech. Lett., 5, pp. 297–300, (1993).

While the wall-plug efficiency of diode lasers is high, sources that directly generate many watts of optical power often require many more watts of electrical power just to cool them. For a sensing application one must therefore balance the requirement for multiple watts of optical power with the desire for a compact and portable device that only consumes a small amount of electrical power.

One solution to this problem relies on using light trapped inside an optical cavity. An optical cavity or resonator consists of two or more mirrored surfaces arranged so that incident light may be trapped, bouncing back and forth between the mirrors. In this way, the light inside the cavity may be many orders of magnitude more intense than the incident light. This general solution is well known and has been exploited in various ways, such as for nonlinear frequency conversion (see, for example, Yariv A., *Introduction to Optical Electronics*, 2nd Ed., Holt, Rinehart, and Winston, N.Y., 1976, Chapter 8), and most widely for spectroscopy, such as is described in Demtroder, W., *Laser Spectroscopy*, springer-verlag, Berlin, 1982, pp. 390–395.

The extension of this solution to chemical sensing relies on the interaction of the intracavity light and the chemical analyte to generate an optical signal. The optical signal may usually be coherent or incoherent, and need not necessarily be at the same frequency as the intracavity light. The magnitude of the optical signal is determined by the amount of chemical analyte present and the intensity of the intracavity light. This technique has been applied to gas monitoring where the optical signal is generated through spontaneous Raman scattering. See, for example, U.S. Pat. No. 4,648,714, "Molecular Gas Analysis by Raman Scattering in Intracavity Laser Configuration," Benner, et al., 10 Mar. 1987.

In all of the previously mentioned methods the optical gain medium (such as a helium neon discharge tube) is within the optical cavity. For a typical diode laser the cavity mirrors are deposited directly on the diode gain medium itself. For some applications, however, such as frequency tuning and linewidth narrowing, one or both of the diode's facets is anti-reflection coated and the diode is operated inside an optical cavity that is defined by mirrors that are external to the diode. While a diode gain media may be operated inside such a cavity, the low damage threshold of the diode's emission facet severely limits the amount of power buildup. In other words, if the diode is placed within the cavity, one cannot allow the power to build up so much that the diode itself is damaged, yet the maximum permissible power is often too little to allow for efficient and simple sensing schemes.

To overcome this limitation while still generating a large optical field, the diode laser may be placed outside of a separate high finesse optical cavity, in which the diode laser radiation is trapped. This separate cavity is referred to below as a "build-up" cavity. Diode lasers, however, emit coherent radiation with an optical bandwidth that is much larger than that of a high finesse build-up cavity. To achieve substantial amplification of diode laser radiation in a build-up cavity the diode laser must bet forced to emit coherent radiation with a linewidth that approaches or matches that of the cavity.

There are several well-known techniques for reducing the bandwidth of diode lasers. For example, active, all-electronic frequency locking of diode lasers may be used. This technique, however, requires very fast servos, with bandwidths up to and even greater than 20 MHz, and a large degree of optical isolation of the diode laser from the cavity. Passive locking has important advantages over active all-electronic locking; for example, the necessary electronic control is greatly reduced, especially if narrow-band radiation is required, and optical isolators may not be needed.

As an alternative, substantial linewidth reduction can be achieved with optical feedback schemes. For example, Dahmani et al., in "Frequency stabilization of semiconductor lasers by resonant optical feedback," Opt. Lett., 12, pp. 876–878 (1987), reported passive optical locking of a diode laser to a build-up cavity. In this technique, light from a diode laser is directed into a build-up cavity and if the light frequency is matched to a cavity resonance frequency then the light is trapped. A portion of the trapped light is then directed back into the diode laser to act as a passive feedback mechanism, which locks the frequency of the low-finesse diode laser to that of the high-finesse build-up cavity.

Tanner et al., in "Atomic beam collimation using a laser diode with a self-locking power buildup cavity," Opt. Lett., 13, pp. 357–359 (1988), describe a self-locking, power-buildup cavity that generates a thousand-fold more light inside the cavity than was incident, but they exploit this intense intracavity light field only for optical pumping of cesium atoms. This technique, however, was recently applied to visible diode lasers, as is described by Simonsen, H. R., in "Frequency noise reduction of visible InGaAlP laser diodes by different optical feedback methods," IEEE J. Quant. Elec., 29, pp. 877–884 (1993).

A shortcoming of the systems described by Dahmani et al., Tanner et al., and Simonsen is that they all employ weak optical locking: only a very minute portion of the light in the build-up cavity is fed back to the diode laser. The disadvantage of the weak optical locking technique, however, is that it still requires careful electromechanical control of both the magnitude and phase of the light fed back to the diode laser. This is discussed, for example, in U.S. Pat. No. 4,907,237, "Optical Feedback Locking of Semiconductor Lasers," Dahmani, B., et al., 6 Mar. 1990; Hemmerich, A., et al., "Second-harmonic generation and optical stabilization of a diode laser in an external ring resonator," Opt. Lett., 15, pp 372–374 (1990); and Buch, P., and Kohns, P., "Optically self-locked semiconductor laser with servo control for feedback phase and laser current," IEEE J. Quant. Elec., 27, 1863 (1991).

A self-locking power build-up cavity has also been used specifically for nonlinear generation of intense amounts of coherent radiation. The use of low to moderate (<1%) feedback from a build-up cavity to optically lock the laser diode to the cavity is described, for example, in the article by Hemmerich, et al. that is mentioned above, and also in Dixon, G. J., Tanner, C. E., and Wieman, C. E., "432-nm source based on efficient second-harmonic generation of GaAlAs diodelaser radiation in a self-locking external resonant cavity," Opt. Lett., 14, pp 731–733 (1989); and U.S. Pat. No. 4,884,276, "Optical Feedback Control in the Frequency Conversion of Laser Diode Radiation," Dixon, et al., 28 Nov. 1989.

This concept is taken further by W. Lenth and W. P. Risk in U.S. Pat. No. 5,038,352, "Laser System and Method Using a Nonlinear Crystal Resonator," 6 Aug. 1991, in which they teach that the use of an anti-reflection (AR) coated diode laser and strong (10%–50%) feedback increases the locking stability. Furthermore, W. J. Kozlovsky, together with Lenth and Risk, reported in "Resonator-enhanced frequency doubling in an extended cavity diode laser," in *Proceedings of the Compact Blue-Green Lasers Topical Meeting*, New Orleans, La., Optical Society of America, February 1993, p. PD2-1, how they employed strong (3%) optical feedback to an AR-coated diode laser and added a dispersive element that reflected light emitted from the build-up cavity back through the cavity and into the diode laser. The dispersive element added frequency stability.

A passive all-optical frequency locking technique for a diode laser is simpler and more stable than either all-electronic or weak-optical-feedback locking because it eliminates the need for sophisticated electronic control of the diode laser or of a light field. To ensure that the diode laser remains stably locked to the build-up cavity it is essential that the dominant optical feedback into the diode gain medium should be from the build-up cavity rather than from any other source, for example, from reflection of light from the diode laser emission facet back into the diode gain medium.

Typically, the diode emission facet is anti-reflection coated, and the whole system may be viewed as a regular solid-state laser with an intracavity etalon. The more light that is fed back to the diode laser from the build-up cavity, the higher is the reflectivity of the diode emission facet that permits stable optical locking.

of all the previously mentioned methods the only two that employ all-optical locking with large feedback are those disclosed by Lenth and Risk (U.S. Pat. No. 5,038,352), and by Kozlovsky et al. Neither of these methods, however, is well suited for sensing applications: it is essential for the stated purpose of these systems to halve the wavelength of the incident light, in particular, to turn near infra-red light into blue.

As Siegman describes in Lasers, University Science Books, Mill Valley, Calif., 1986, pp. 428–31, the power that can be generated inside an optical build-up cavity is inversely proportional to the optical loss of the cavity. The optical loss is approximately the sum of the optical losses of all the individual intracavity elements such as mirrors.

A structure that is optimal for coherent generation of radiation necessarily produces a useful amount of output radiation (see Kozlovsky and Lenth). This conversion also acts as an additional loss mechanism for the intracavity radiation and reduces the amount of power that can be generated in the optical cavity. The non-linear crystal used in systems such as Lenth's and Kozlovsky's has additional absorption losses, which act to reduce the cavity finesse; both these substantial loss mechanisms are essential for coherent generation of radiation. For intracavity chemical sensing, however, in particular for Raman gas sensing, one requires as large an intracavity power as possible, consequently, any structure that incorporates unnecessary and substantial losses is unsuitable for sensitive intracavity chemical sensing. A structure that is best suited for chemical sensing would be a build-up cavity that has as low an optical loss as practical, so that as little an amount of light as possible escapes the cavity and is thus fundamentally different from that described by Lenth and Kozlovsky.

In the context of external cavity semiconductor lasers, it is well known that anti-reflection coating of the diode output facet and strong optical feedback are essential for stable performance. See Rong-Qing, H., and Shang-Ping, T., "Improved rate equations for external cavity semiconductor lasers," IEEE J. Quant. Elec., 25, pp. 1580–1584, 1989. These laser systems have been employed for intracavity spectroscopy, see Baev, V. M., Eschner, J., Paeth, E., Shuler, R., and Toschek, P. E., "Intra-cavity spectroscopy with diode lasers," Appl. Phys. B., B55, pp. 463–477, 1992, but, as discussed above, the cavity finesse and thus intracavity power are deliberately kept low to prevent optical damage to the laser facet of the diode. These devices are therefore unsuitable for sensing applications that rely on high intracavity power.

For chemical sensing, what is needed is a compact system that combines high intracavity power with low required input power and that locks passively and optically, thereby doing away with a need for complicated and expensive locking circuitry.

SUMMARY OF THE INVENTION

A semiconductor laser power build-up system includes a semiconductor laser that has an emission facet and outputs an incident light beam. An optical resonance cavity is defined between a primary, entrance reflective element and one or more secondary reflective elements and has an intracavity light beam along an intracavity beam path. A return light beam consists of a portion of the intracavity light beam that is transmitted through the entrance reflective element and that is coincident with but oppositely directed relative to the incident beam. The laser is wholly optically locked to the cavity and the intracavity beam passes substantially without loss within the cavity.

The invention preferably further includes a wavelength-determining element such as a grating or an etalon in the incident beam path between the laser and the first reflective element.

The emission facet preferably has a reflectivity less than 0.01, or even less than 0.0001, for example, by means of anti-reflection coating. Feedback of the return beam into the laser through the emission facet may be strong, for example, greater than 3%.

The invention preferably also includes an optical shaping device in the incident light path for the purpose of impedance matching.

A preferred application of the system is for the detection of chemicals in a sample. The sample is thereby positioned in an interaction region of the cavity and a detection system is positioned for sensing a predetermined characteristic (such as Raman-scattered light) of the sample within the interaction region. The intracavity beam passes substantially without loss within the cavity except for interaction with the sample.

A further aspect of one embodiment of the invention is that the semiconductor laser is a high-power diode laser with an unmodified emission facets, In this case, the invention provides for driving the diode laser with a current that is less than the bare-diode threshold current.

DETAILED DESCRIPTION

The invention is described primarily with reference to its use in sensing gases since it is particularly well-suited for this use. The invention may, however, also be used to sense liquids; necessary modifications are discussed below.

Figure 1:
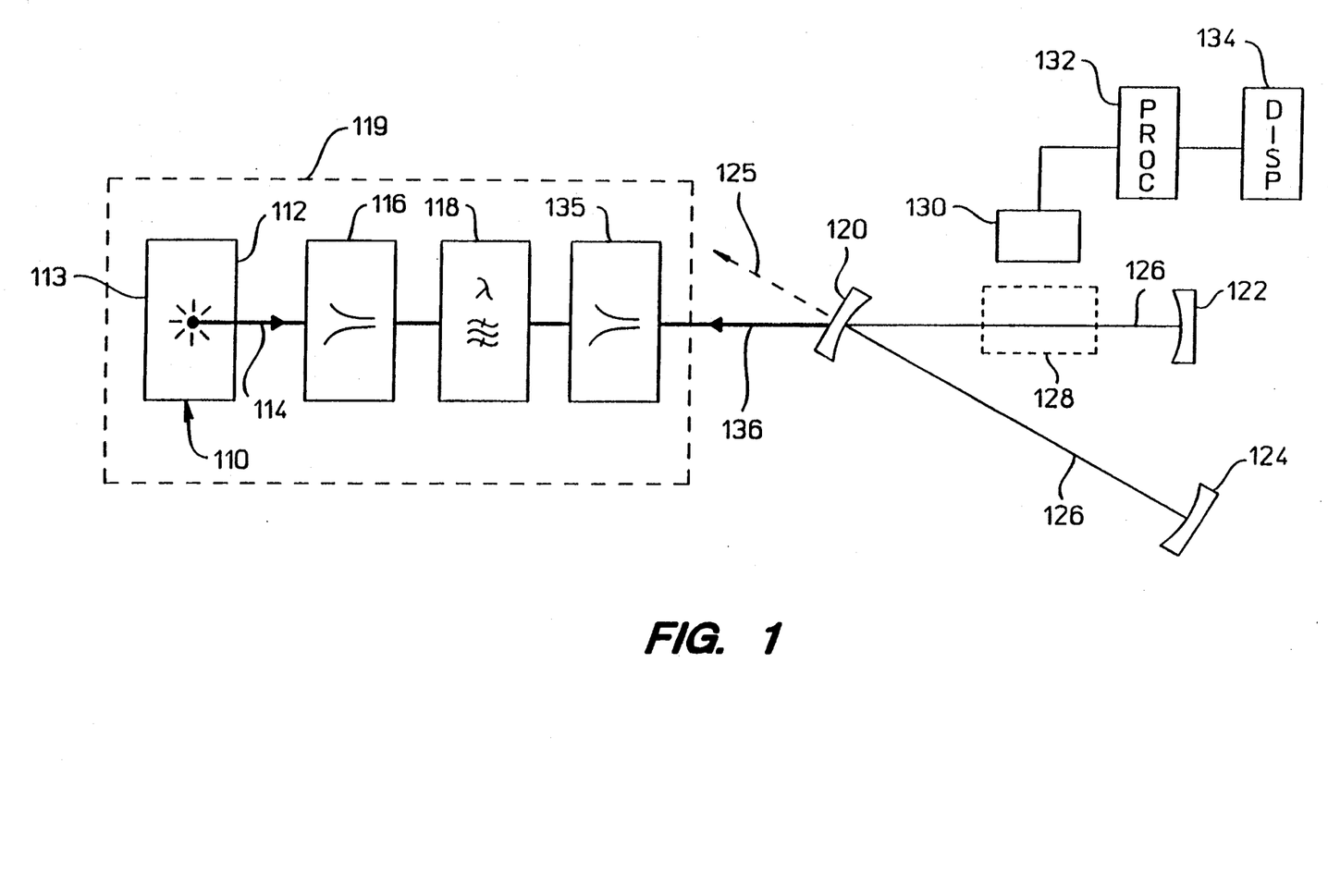
FIG. 1 illustrates a sensing system according to the invention, with an optically locking semiconductor light source that is external to a power build-up cavity.

A first and preferred embodiment of the invention is illustrated in FIG. 1. A diode laser forms a light source 110, which has an emission facet 112 and a back facet 113. The light source emits a light beam 114. Examples of commercially available devices that are suitable as the light source 110 include the single-longitudinal mode and index guided (SLM-ID) lasers of the types Toshiba 9215, Hitachi HL6714G, or Philips CQL601D as well as high-power, broad-area devices such as Philips CQL602D.

Additionally, the back facet 113 of the light source 110 could have a low reflectivity (for example, as a result of anti-reflection coating), in which case a small mirror should be placed behind the back facet of the light source to reflect light emitted from the light source through the back facet back into the light source along line 114. The advantages of this arrangement are that one can then modulate the system by varying the position of this additional mirror and one may place optical elements (described below) between the back facet 113 and this additional mirror. This embodiment is described in greater detail below with reference to FIG. 2.

The circuitry necessary to power the light source 110 is conventional and is not shown. Of note, however, is that some of the suitable semiconductor laser devices, including those listed above, will typically draw no more than about 100 mW of power, with little or no additional power needs for cooling devices. Furthermore, other semiconductor devices such as an anti-reflection coated diode laser or a superluminescent diode may be used as the light source 110.

The light source 110 emits a light beam 114, which is spatially shaped in a known manner by a conventional optical shaping system 116 to ensure proper impedance matching. A wavelength-determining element 118 is included in the path of the light beam 114 to set the value of the operating wavelength and to limit the diode-cavity average optical bandwidth. An additional conventional beam-shaping system 135 may be necessary if the beam 114 that exits the shaping system 116 is not spatially optimized both for the wavelength-determining element 118 and impedance-matching into the build-up cavity. Using well-known fabrication techniques, the light source 110, the optical shaping system 116 (and 135, if included), and the wavelength-determining element 118 may be mechanically incorporated into a single light source unit, as is indicated by the dashed line 119. The optical shaping system 116 and the wavelength-determining element 118, which acts as an optical, tunable, bandpass filter, may be conventional devices whose structure and operation are well known. The light beam 114 forms an incident beam, which is indicated in FIG. 1 by a right-pointing arrow.

The light beam 114 impinges on a build-up cavity, which comprises reflective elements such as mirrors 120, 122, and 124, and generates an intracavity beam 126. The mirror 120 is preferably tilted (not perpendicular to the direction of the light beam 114) to prevent direct reflection of beam 114 back into the light source, which would reduce the ability of the light source to lock onto the intracavity beam 126. The portions of the light beam 114 that are reflected back by the tilted mirror 120, and the very small portion of beam 126 (from mirror 124) that the mirror 120 transmits, are indicated by the dashed arrow 125.

The beam 126 passes through a sample 128 (which is contained in any conventional cell or other holding structure) and the optical signal generated by the interaction of beam 126 with sample 128 is detected by a conventional detection system 130, which may detect, for example, Raman-scattered light. The output from the detection system forms an input signal to conventional processing circuitry 132, which determines the presence or amount of the substance of interest in the sample 128 using known analytical techniques. The results of the analysis by the processor may be passed on to further processing circuitry (not shown) or may be displayed on a conventional display device 134.

A small portion of beam 126 leaks through the entrance mirror 120 as a return beam 136. The return beam 136 coincides with the incident beam 114 but in the opposite direction (indicated as a left-pointing arrow). From the entrance mirror 120, the return beam 136 passes through the wavelength-determining element 118, the optical shaping system 116 (and 135, if included), and back into the light source 110 through its emission facet 112.

The invention allows the power of the intracavity beam 126 to be many orders of magnitude larger than the power of the incident beam 114 without the need for any electronic control of the light source other than a conventional, stable current source (not shown). An additional advantage is that a small and inexpensive light source results in a very large generated optical signal from the sample. This is accomplished by selecting parameters of the emission facet 112, the optical shaping system 116 (and 135, if included), the wavelength-determining element 118, and the mirrors 120, 122, 124 to maximize the power of the intracavity beam 126, as described below.

To ensure the maximum intensity of the intracavity beam 126, most of the output from the light source 110 should be resonant (of the same frequency) with the build-up cavity; in other words, the light source should be optically locked to the cavity. According to the invention, this is achieved by ensuring that the dominant feedback into the light source 110 is the return beam 136. The main problem in this respect is the reflection of the beam 114 by the emission facet 112 back into the light source 110.

According to the invention, any of several methods may be used to ensure that the leaked beam 136 is the dominant feedback. If the diode laser 110 is chosen to be a SLM-ID device of the type Toshiba 9215, Hitachi 6714G, or Philips CQL601D, then it is usually operated well above the bare-diode threshold current (the current threshold for an unmodified diode laser operating in isolation) for optimum power build-up. Calculations and experiments have indicated that the return beam 136 has a feedback in a range of 1%–50% to ensure power stability. To ensure that beam 136 is the dominant feedback, the reflection of beam 114 from facet 112 must be at least 10–100 times less intense than beam 136. In this case, the emission facet 112 should have a reflectivity of approximately 0.01 or 0.001, and it should preferably be between 0.001 and 0.0001 in order to ensure stable locking. In one prototype of the invention, the feedback from the cavity was estimated to be between 10% and 20%, and for stable locking the optimal reflectivity of the emission facet of a Hitachi 6714G diode laser was in the range 0.001–0.0001.

One way to achieve these low reflectivities is by using anti-reflection coating of the facet; this technique for reducing reflectivity is well known (see, for example, Eisenstein, G. and Stulz, L. W., "High quality anti-reflection coatings on laser facets by sputtered silicon nitride," Appl. Opt., 23, 161 (1984)). According to the invention, one advantage of the anti-reflection coating on the diode laser is that it eliminates the conventional need for additional electronic circuitry to phase-lock the diode to the cavity.

Alternatively, a high power SLM-ID or other diode laser may be employed without the alteration of the emission facet. If the feedback is large enough, the diode-cavity system lasing will occur below the bare-diode threshold current. Once the diode-cavity system is lasing, the optical reflection from the emission facet must be low enough not to deplete the diode gain. As the diode current is raised closer to the bare-diode threshold, the emission-facet reflection may begin to deplete the diode gain, which in turn leads to power instability.

The limit in power build-up is therefore determined by the amount of feedback and emission-facet reflectivity. One advantage of the invention is that it can operate without any such feedback-limiting devices such as variable attenuators or optical isolators. For example, a high-power diode may be operated well below its bare-diode current threshold and still have enough gain to lase when light is fed back from the build-up cavity. Such diodes are described in Ueno, et al., "30-mW 690-nm high-power strained-quantum-well AlGaInP laser," IEEE J. Quant. Elec., 29, 1851 (1993); and Arimoto, et al., "150 mW fundamental-transverse-mode operation of 670 nm window laser diode, IEEE J. Quant. Elec., 29, 1874 (1993). One prototype of the invention used an SLM-ID laser at 680 nm with a high reflector back facet and an emission facet with a 10% reflectivity. This diode was operated 10mA below the bare-diode threshold and still achieved suitable stable power build-up because the effective reflectivity of the build-up cavity exceeded 10%.

Other sources of reflection back into the diode laser should be minimized. For example, the optical shaping element 116 (and 135, if included) and the wavelength-determining element 118 should be anti-reflection coated or simply tilted slightly.

To maximize the intensity of beam ].26 the optical system 116 (and 135, if included) includes components such as lenses or prisms that shape the beam 114 and spatially match the beam 126. In addition, the wavelength-determining element 118 may operate optimally with particular incident beam properties. For example, if element 118 is an etalon, then an optimal incident beam should be non-divergent in order to transmit the maximum amount of light. In this case, the optical element 116 optimally shapes beam 114 for transmission through element 118, and the optical element 135 spatially matches this transmitted beam to the beam 126. Note that element 118 may also shape the beam 114, for example, if element 118 is a diffraction grating. For certain applications, slightly sub-optimal performance of element 118 is acceptable, in which case the beam-shaping functions of element 135 may be incorporated into element 116.

Both the components and techniques of such beam-shaping are well understood in the art of optics and conventional components may be used. The shape of beam 126 is determined by the build-up cavity formed by mirrors 120, 122, and 124, and can be one or many transverse electromagnetic cavity modes.

There are many options for the design of the optical shaping system 116 (and 135, if included) well known to those skilled in the art. Examples of suitable configurations include:

(a) a single lens or multi-element lens to both collect and focus the beam 114 into the build-up cavity;
(b) a single lens or multi-element lens to collimate the beam 114, and an additional lens to focus the beam 114 into the build-up cavity, in which case the position and focal length of the additional lens are chosen to impedance match beam 114 into the build-up cavity;
(c) same as (b) plus two cylindrical lenses to circularize the beam 114;
(d) same as (b) plus an anamorphic prism pair to circularize the beam 114;
(e) same as (c) or (d) plus an astigmatism correction lens; and
(f) a GRIN lens to collimate the beam 114 and a second lens to focus the beam into the build-up cavity.

All of the designs (a)–(f) image the beam 114 into the build-up cavity with differing efficiency. To compensate for this effect the diode current may need to be changed in order to generate the same optical power.

One should choose the imaging system that has the highest efficiency to ensure that the beams 126 and 136 are the most intense at a given diode laser current. This choice will depend on the specific geometries of a given application, as well as on cost, and can be made using well-known experimental and theoretical techniques.

The build-up cavity has a "comb" of resonant frequencies spaced by $D=c/2L$, where D is the mode spacing in Hertz, c is the speed of light, and L is the round-trip path length of the build-up cavity. For example, if $L=30$ cm, then $D=0.50$ GHz. If the specific sensing application requires that the intracavity beam 126 should contain one or a few cavity modes, then a wavelength or frequency-determining element 118 must be employed.

A typical diode laser gain medium has substantial gain over a width of approximately 3 THz (or 5 nm at 670 nm), so that many cavity frequencies may lase and build-up simultaneously or separately in a random fashion. The purpose of the wavelength-determining element 118 is to limit the number of build-up cavity modes that may lase. The number of lasing modes is determined by the bandpass of the wavelength-determining element 118, and may be as few as one. The transmission of the wavelength-determining element 118 must be large to ensure that the intensities of beams 126 and 136 are as large as possible. In various working prototypes of the invention, transmissions of 80% and greater were used.

The wavelength-determining element 118 includes suitable filtering elements, which may be dispersive, absorbing, or a combination of both. An optical filter or absorber with a narrow bandpass may be used to heavily attenuate a large number of modes, thereby preventing them from building up. Examples of suitable filters include dielectric-stack bandpass filters, etalons, Lyot filters, and acousto-optic filters. The element 118 may be incorporated into the back facet 113 of the light source 110, for example, by depositing a dielectric stack reflector or some other known coating on the back facet 113. In this case, the action of facet 113 is to reflect only a predetermined, appropriately narrow band of frequencies back along the path of the beam 114, thereby limiting the number of cavity modes that may lase.

Dispersive elements, for example gratings and prisms, deflect a light beam by a certain angle, which depends on the frequency of the light. Thus, only a few build-up cavity modes can be generated by beam 126 and supply a beam 136 that returns to the diode 110. In this case, the number of modes that may build up is determined by the dispersion of the wavelength-determining element 118 and the distance between this element and the build-up cavity.

An example of a suitable diffractive element is a transmission grating with 1800 grooves per mm with a transmission efficiency of 80%. A reflection grating may also be used; in a prototype of the invention, a grating with 2400 grooves per mm and a reflection efficiency of 90% was employed. The beam 114 may be deflected (or reflected) when it passes through the wavelength-determining element 118.

Figure 2:
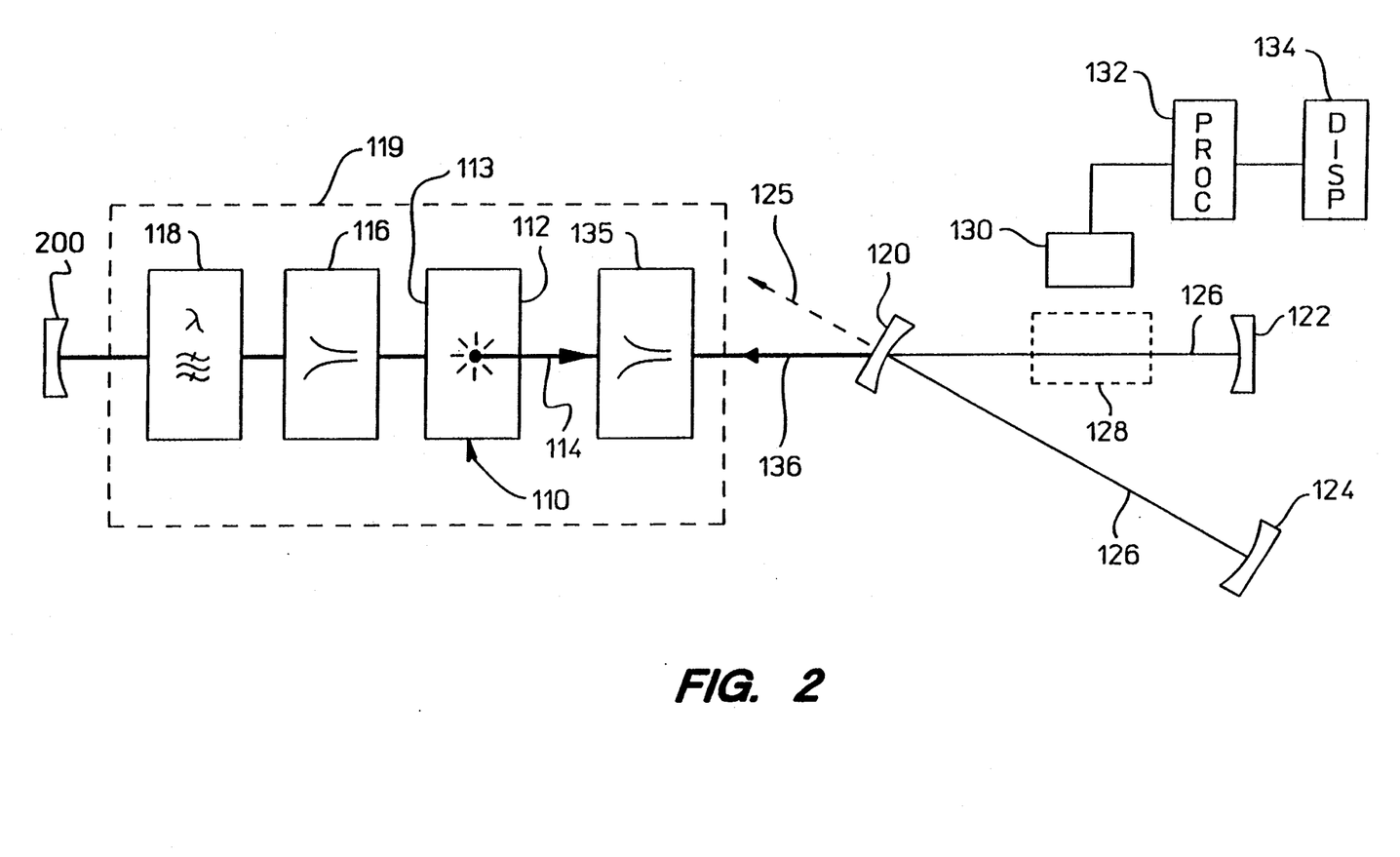
FIG. 2 illustrates a second embodiment of the invention, in which an external mirror reflects light back into the light source through an anti-reflection coated back facet.

FIG. 2 illustrates a second embodiment of the invention, in which the back facet 113 is AR-coated similar to the emission facet 112, and an additional mirror 200, reflects the beam 114 back into the light source 110 through the back facet 113. The wavelength-determining element 118 will operate in the same manner as described above if it is then placed between the mirror 200 and the back facet 113. Additionally, the beam-shaping optics 116 may be necessary to shape the beam 114 for optimal performance of the element 118. In this case, it too will be placed between the mirror 200 and the back facet 113, preferably (but not necessarily) between the wavelength-determining element 116 and the back facet 113.

If the frequency window (or bandpass) transmitted by the wavelength-determining element 118 can be tuned then the average frequency of beam 126 may also be tuned. The tuning range is limited ultimately by the gain bandwidth of the diode laser 110. Examples of tuning include rotating either the grating or an etalon. In the invention, the wavelength-determining element 118 is placed between the laser 112 and the cavity; the element 118 may then be incorporated into the back facet 113 of the light source, or may be placed between the light source and the external mirror 200. The position of the element 118 in this invention is therefore fundamentally different from that described by, for example, Kozlovsky: the cavity design in the invention permits negligible amounts of light to pass through the mirrors 122 and 124.

Each of the mirrors 120, 122, and 124 has a radius of curvature and relative spacing chosen using conventional criteria to optimize the intensity of the beam 126, as well as satisfying any specific sensing application needs. The value of the mirror reflectivities determines the reflectivity finesse of the optical cavity and thus the intensity of beams 126 and 136; the actual value will depend on a given application and can be determined by experiment or calculation using known techniques, in which a dominant consideration is impedance matching. Calculations have indicated that an optimum impedance-matching mirror 120 should have a loss (including transmission, absorption, and scattering losses) in the range 50-300 parts per million (ppm) and that the loss for the secondary mirrors 122, 124, should be in the range 1-100 ppm. Two examples of suitable mirror transmission losses, which were used in prototypes of the invention, are if all three mirrors have transmission losses of 12 ppm, or if the mirror 120 has a loss of around 100 ppm and mirrors 122 and 124 both have losses of about 12 ppm. Compared with systems that use gratings and other frequency-locking devices after the cavity in the light path (beyond the cavity's "end mirror"), the end mirrors 122, 124 in the invention can therefore be several orders of magnitude more reflective, and increase the invention's efficiency by greatly reducing loss.

The optimum radii of curvature for the mirrors 120, 122, and 124 will also depend on the given application and can be determined experimentally or theoretically. In one prototype of the invention, the radius of curvature for all the mirrors 120, 122, and 124, was 17 cm. The distance between the mirrors 120 and 122, and between the mirrors 120 and 124, should also be chosen in any conventional manner to form a stable cavity mode; in the prototype of the invention just mentioned, the spacing between the mirrors was 14 cm.

In the case that the sample 128 contains many gases, which fill the optical beam path of the cavity, then the angle between the two arms of the V-shaped build-up cavity formed by mirrors 120, 122, and 124 should be small (for example, less than 20 degrees); otherwise, changes in refractive index due to gas changes will affect the refraction of the beam 114 as it passes through the entrance mirror 120. Other mirror positions and radii of curvature could be suitable for different applications, for example having mirrors 124 and 120 very close to each other so that they could fit into one small solid mount.

The detection system 130 incorporates known optics suitable for collecting the generated signal and a detector for detecting the collected signal. The position of the detection system 130 is determined by the position of the optics employed in the detection system 130 and may be next to the sample 128 or at any other convenient location. The placement of the detection system will normally depend on the application, and can be determined simply by experimentation or knowledge of the properties of the optical signal (such as Raman scattering or fluorescence) one expects the sample to give off.

The three-mirror, V-shaped build-up cavity defined by mirrors 120, 122, and 124 is not the only suitable cavity configuration; other configurations are described below. A common feature of the build-up cavities used in the invention, however, is that they ensure a large optical feedback into the diode laser. In general, one should choose a cavity configuration that provides a single return beam 136 that originates from the intracavity beam 126. A V-shaped cavity achieves this because any non-resonant incident beam will be reflected by the input mirror 120 and not get back into the diode laser. Another way to accomplish this would be by using additional extra-cavity mirrors, as would be necessary in a ring cavity. Preferable examples where an additional element is not necessary are shown in FIG. 3 and 4.

Figure 3:
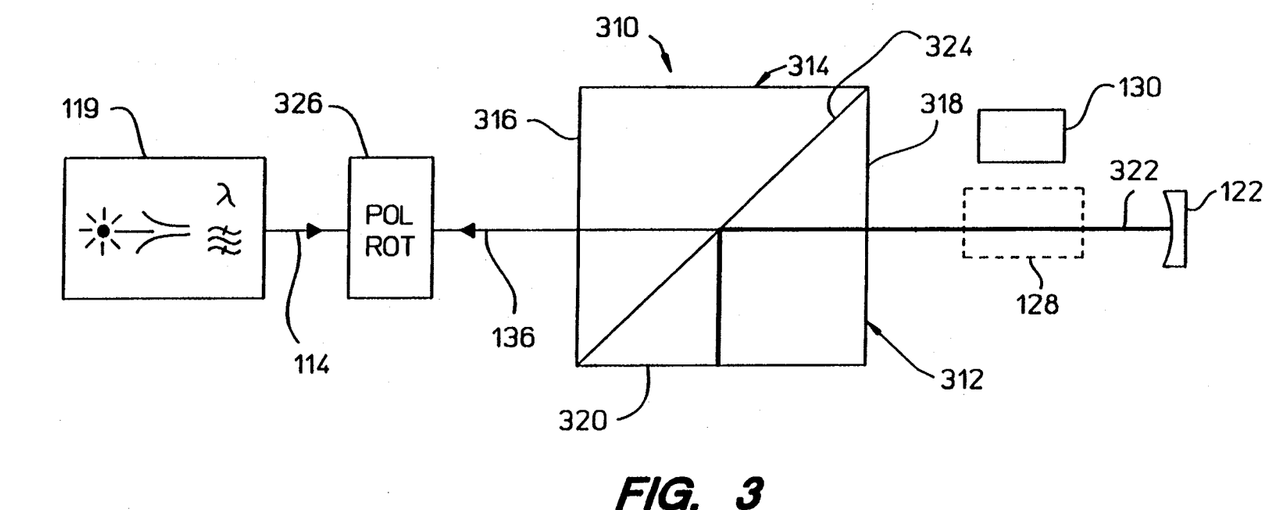
FIG. 3 illustrates a third embodiment of the invention in which an optical cube replaces certain mirrors in the embodiment shown in FIG. 1.
Figure 4:
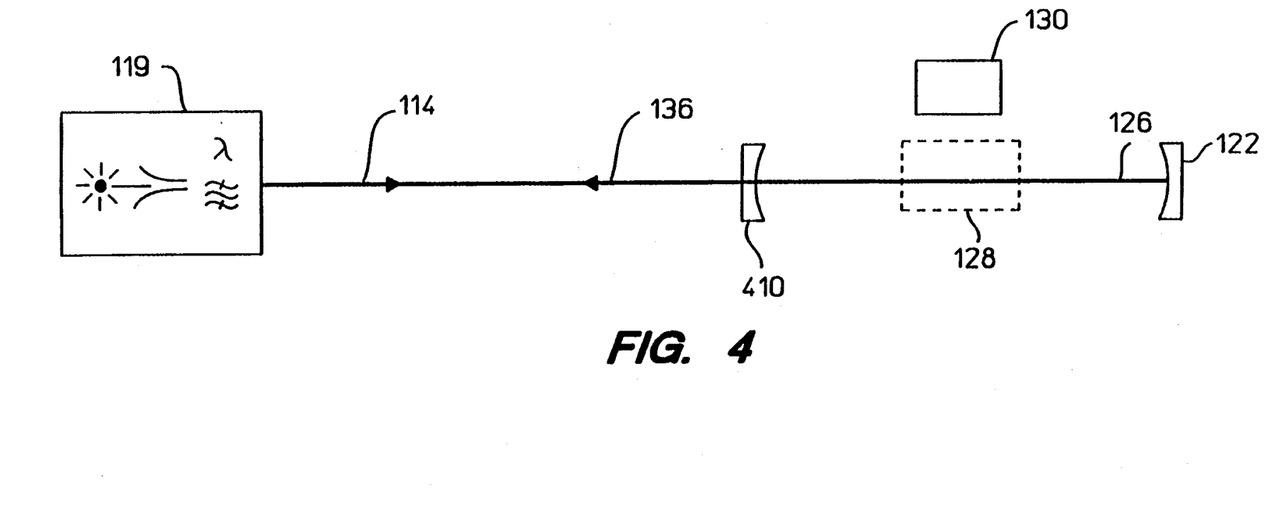
FIG. 4 illustrates a fourth embodiment of the invention, in which the cavity has a linear configuration.

FIG. 3 illustrates a third embodiment of the invention, in which an optical cube 310 replaces the two mirrors 120, 122 shown in FIG. 1. Features common to the embodiments of both FIG. 1 and FIG. 2 retain the reference numbers they have in FIG. 1. In particular, the combined light source, shaping optics and wavelength-determining element are labelled 119, although, as in the first embodiment, they need not be integrated into a single unit.

The optical cube 310 is constructed in a known manner by optically cementing together two prisms 312 and 314; in one prototype, two right prisms were used. One face 320 of prism 312 (the face that is substantially parallel to the incident beam 114 and the return beam 136) is highly reflective and therefore performs the function of a mirror, while faces 316 and 318 (the faces that are substantially perpendicular to the beam at the entrance and exit surfaces, respectively, of the cube 310) are anti-reflection coated. To generate an intracavity beam 322 with as much intensity as possible, the surface or face 318 must have as low a loss as possible. A third face 324 of prism 312 (the face at the contact surface between the two prisms) is also highly reflecting and also serves to function as a mirror, and the value of the reflectivity is chosen in any known manner to impedance-match the input beam 114 into the cavity.

The optical cavity is formed by the three mirrors 320, 324, and 122. The advantage of this construction is that two optical elements are combined into one piece. Care must be taken, however, to reduce the birefringence of the prism material. A polarization-rotation element 326, preferably a half-wave plate, may be required if the beam 114 is polarized, and may be adjusted using well-known conventional techniques.

FIG. 4 illustrates a fourth embodiment of an optical cavity according to the invention, once again with a suitable light source 119. In this embodiment, the configuration of the cavity is linear, with an entrance mirror 410 whose reflectivity impedance matches the beam 114 into the cavity, which is formed by mirrors 410 and 122.

In this case there is a reflection from the mirror 410 back exactly along beam 136, which comprises two components. The first reflected component consists of light that is at a resonant frequency of the cavity, and the second component consists of the light at all other incident frequencies. The magnitude of the first resonant component is determined both by the parameters (curvature and reflectivity) of mirrors 410 and 122 and by the degree of spatial overlap between the beams 114 and 126. The magnitude of the first reflected component can be viewed as the amount of intracavity light that leaks back through mirror 410, whereas the magnitude of the second component is determined by parameters (curvature and reflectivity) of mirror 410 alone. Both of these reflected components lead to feedback into the optical source; the magnitude of this feedback is additionally determined by the beam-shaping optics.

If it is similar in magnitude to the first resonant feedback path, the second feedback path will compete for optical gain in the light source and will lead to power instability. To force the light source to stably lock to the first resonant feedback reflection, one must ensure that the magnitude of the second feedback is approximately ten or more times smaller than the first resonant feedback. In this case, for example, the drive current for the optical source may be chosen to supply only enough gain so that the system is above lasing threshold for the first resonant feedback only. A limitation with this solution is that the gain of the optical source cannot be increased further due to onset of power instability; this therefore limits the amount of power that can be built up in the cavity formed by mirrors 410 and 122. Another, and preferred, solution is to include the wavelength-determining element (in FIG. 4, it is included in the unit 119) and to place it between the light source and the mirror 410.

The frequency spacing between resonant modes of an optical cavity is inversely proportional to the mirror separation. If the distance between the light source (or more exactly the high reflector of the light source, that is, either the back facet 113 or the mirror 200) and the mirror 410 is smaller than the distance between the mirrors 410 and 122, then the frequency difference between the resonant modes in the former is larger than in the latter. For example, if a narrow-band filter were used with a bandpass less than the larger of the frequency differences just mentioned, then the second feedback path would be prevented from lasing while the first resonant path would still lase. A similar solution would be possible for the wavelength-determining elements mentioned above, especially when they are implemented as an etalon.

Another way to isolate the non-resonant reflection is through polarization. If a low-loss polarization-rotation element, such as a half-wave plate, is included in the optical cavity, the resonant reflection is out of phase with the non-resonant reflection and may be distinguished by inserting a polarizer between the light source and the cavity. If the light source emits radiation that is substantially polarized then additional polarization-rotation elements may be necessary.

In the illustrated embodiments of the invention, the intracavity beam is shown as passing straight from the entrance reflective element (mirrors 120 and 410 or prism pair 310), through the sample, and on to the end reflective element 122. Although this is the simplest and therefore preferred intracavity light path when the invention is used to sense such physical properties as Raman scattering by the sample, this is not necessary. Instead, the intracavity beam could be directed to one or more intermediate reflective elements, with the sample positioned appropriately relative to the intracavity beam and to the detector 130, as long as the intermediate elements are so highly reflective that the substantially lossless buildup within the cavity is maintained and as long as the geometry of the cavity (spacing and radii of curvature) and its defining reflective elements is adjusted in any conventional manner to ensure that a stable cavity mode is formed.

Such an arrangement might be necessary, for example, in applications in which the intracavity beam is not to pass directly through the sample, but rather in which the sample's identifying characteristic of interest is detected based on some other interaction between the beam and the sample. In any event, the sample will be positioned in some interaction region of the optical cavity, which may be within the cavity itself (as is shown in the figures). Furthermore, the optical loss of the sample should be less than that of the cavity mirrors. If this is not the case, the mirror reflectivities should be chosen to optimize impedance matching into the cavity.

In the various embodiments of the invention, there is no need to deliberately include any loss mechanisms such as non-linear crystals in the cavity. One great advantage of all the embodiments of the invention is that they make possible substantially lossless reflection over the entire spectrum of the laser diode emission. Indeed, there is no inherent structural loss within the cavity at all, and the only "loss" will be that associated with the energy absorbed, converted, or scattered by the sample, which is of course the energy that is detected by the detection system 130.

We claim:

1. A system for detecting chemicals in a sample comprising:
   A) a semiconductor laser that has an emission facet and that outputs an incident light beam along an incident beam path;
   B) an unimpeded optical resonance cavity that is defined between a primary, entrance reflective element and at least one secondary reflective element and further having a comb of resonant frequencies, the unimpeded cavity having an intracavity light beam and a substantially lossless intracavity beam path, the intracavity light beam having frequency components within the comb of resonant frequencies ann extending along the entirety of the intracavity beam path;
   C) a reference light beam that consists of a portion of the intracavity light beam that is transmitted through the entrance reflective element and that is coincident with but oppositely directed relative to the incident light beam, the semiconductor laser being wholly optically locked to the optical resonance cavity thereby;
   D) means within an interaction region disposed along the intracavity beam path for receiving the sample, thereby positioning the sample to be intersected by the intracavity light beam; and
   E) detection means positioned adjacent to the interaction region for sensing a predetermined characteristic of the sample within the interaction region as a response to the intersection of the sample with the intracavity light beam.

2. A system as defined in claim 1, further including a wavelength-determining element in the incident beam path between the laser and the entrance reflective element.

3. A system as defined in claim 2, in which the wavelength-determining element is a grating.

4. A system as defined in claim 2, in which the wavelength-determining element is an etalon.

5. A system as defined in claim 1, in which the entrance reflective element has a loss in the range 50–300 parts per million and the secondary reflective elements have losses in the range 1–100 parts per million.

6. A system as defined in claim 1, in which feedback of the reference beam into the laser through the emission facet is greater than 3%.

7. A system as defined in claim 1, in which the emission facet is anti-reflection coated.

8. A system as defined in claim 7, in which the emission facet has a reflectivity less than 0.01.

9. A system as defined in claim 8, in which the emission facet has a reflectivity less than 0.0001.

10. A system as defined in claim 1, further including an optical shaping and impedance matching device in the incident beam path.

11. A system as defined in claim 1, in which the entrance reflective element is angled so as to be non-perpendicular to the incident beam.

12. A system as defined in claim 1, further including a back mirror and in which:
    A) the semiconductor laser has a back facet; and
    B) the back mirror reflects light that exits the back facet back through the back facet and into the semiconductor laser.

13. A system as defined in claim 12, further including a wavelength-determining element that is positioned between the back mirror and the back facet.

14. A system as defined in claim 13, in which the back facet is anti-reflection coated.

15. A system as defined in claim 14, further including optical shaping and impedance matching means for optically shaping and impedance matching light emitted from the semiconductor laser.

16. A system as defined in claim 1, in which the semiconductor laser has a back facet that is coated with a narrow-bandwidth reflective coating.

17. A system as defined in claim 16, in which the narrow-bandwidth reflective coating is a dielectric stack.

18. A system as defined in claim 17, further including optical shaping and impedance matching means for optically shaping and impedance matching light emitted from the semiconductor laser.

19. A method for detecting chemicals in a sample comprising the following steps:
    A) providing an unobstructed light beam path between a first reflective element and at least one second reflective element, including forming a substantially lossless optical resonance cavity having a comb of resonant frequencies;
    B) directing incident light from a semiconductor laser as an incident light beam into the optical resonance cavity;
    C) wholly optically locking the laser to the optical resonance cavity, including a substep of repeatedly reflecting, within the optical resonance cavity, components of the incident light beam having a frequency within the comb of resonant frequencies and including a substep of directing a portion of the incident light beam from the optical cavity into the semiconductor laser;

D) positioning the sample in an interaction region of the optical resonance cavity such that the incident light impinges the sample; and E) identifying chemicals within the sample, including detecting a response of the sample to impingement of the sample by the incident light and utilizing the detecting for measuring a predetermined characteristic of the sample within the interaction region.

20. A method as defined in claim 19, further including the step of feeding back into the laser a return light beam that has at least 3% the intensity of the incident light beam.

21. A method as defined in claim 20, in which the semiconductor laser is a diode laser with an unmodified emission facet, further including the step of driving the diode laser with a current that is less than the bare-diode threshold current.

22. A method as defined in claim 20, further including the step of anti-reflection coating an emission facet of the semiconductor laser.

23. A semiconductor laser power build-up system comprising:

A) a semiconductor laser that has an emission facet and that outputs an incident light beam along an incident beam path;

B) a substantially lossless and optically resonant cavity having an unimpeded light beam path therebetween, including a primary, entrance reflective element and at least one secondary reflective element and further including a reflected light beam having components at frequencies that lie within a comb of resonant frequencies of the optically resonant region, the reflected light beam radiating along the full extent of the optically resonant region; and C) a reference light beam that consists of a portion of the reflected light beam that is transmitted through the entrance reflective element and that is coincident with but oppositely directed relative to the incident beam the laser being wholly optically locked to the optically resonant region thereby.

24. A system as defined in claim 23, further including a wavelength-determining element in the incident beam path between the laser and the entrance reflective element.

25. A system as defined in claim 24, in which the wavelength-determining element is a grating.

26. A system as defined in claim 23, in which the entrance reflective element has a loss in the range 50–300 parts per million and the secondary reflective elements have losses in the range 1–100 parts per million.

27. A system as defined in claim 23, in which the emission facet has a reflectivity less than 0.01.

28. A system as defined in claim 27, in which the emission facet has a reflectivity less than 0.0001.

29. A system as defined in claim 23, in which feedback of the reference beam into the laser through the emission facet is greater than 3%.

30. A system as defined in claim 29, in which the emission facet is anti-reflection coated.

31. A system as defined in claim 23, further including an optical shaping and impedance matching device in the incident beam path.

32. A system as defined in claim 23, in which the entrance reflective element is angled so as to be non-perpendicular to the incident beam.

33. A system as defined in claim 23, further including a back mirror and in which:

A) the semiconductor laser has a back facet; and

B) the back mirror reflects light that exits the back facet back through the back facet and into the semiconductor laser.

34. A system as defined in claim 33, further including a wavelength-determining element that is positioned between the back mirror and the back facet.

35. A system as defined in claim 34, in which the back facet is anti-reflection coated.

36. A system as defined in claim 35, further including optical shaping and impedance matching means for optically shaping and impedance matching light emitted from the semiconductor laser.

37. A system as defined in claim 23, in which the semiconductor laser has a back facet that is coated with a narrow-bandwidth reflective coating.

38. A system as defined in claim 37, in which the narrow-bandwidth reflective coating is a dielectric stack.

39. A system as defined in claim 38, further including optical shaping and impedance matching means for optically shaping and impedance matching light emitted from the semiconductor laser.

* * * * *